United States Patent [19]

Malpass et al.

[11] Patent Number: 4,720,562
[45] Date of Patent: Jan. 19, 1988

[54] NOVEL TITANIUM-CONTAINING REAGENTS FOR METHYLENATION AND ANALOGOUS REACTIONS

[75] Inventors: Dennis B. Malpass, LaPorte; Andrzej M. Piotrowski, Houston, both of Tex.

[73] Assignee: Stauffer Chemical Company, Westport, Conn.

[21] Appl. No.: 939,893

[22] Filed: Dec. 16, 1986

Related U.S. Application Data

[63] Continuation-in-part of Ser. No. 818,589, Jan. 14, 1986, abandoned.

[51] Int. Cl.$^4$ ................................................ C07F 7/28
[52] U.S. Cl. ........................................... 556/27; 546/2; 549/206
[58] Field of Search ............... 556/27; 549/206; 546/2

[56] References Cited

U.S. PATENT DOCUMENTS

| | | | |
|---|---|---|---|
| 2,952,670 | 9/1960 | Fischer | 556/27 X |
| 3,108,973 | 10/1963 | Vandenburg | 556/27 X |
| 3,274,223 | 9/1966 | Feay | 556/27 |
| 3,444,153 | 5/1969 | Fodor | 556/27 X |
| 3,463,743 | 8/1969 | Durst et al. | 556/27 X |
| 3,700,710 | 10/1972 | Mottus | 556/27 X |

OTHER PUBLICATIONS

Tebbe et al., JACS 100 pp. 3611-3613 (1978).
Tebbe et al., JACS 102 pp. 6149-6150 (1980).
Pine et al., J. Org. Chem. V50, 1212 (1985).
Tebbe et al., JACS 101 pp. 5074-5075 (1979).
Tebbe et al., JACS 102 pp. 6876-6878 (1980).

*Primary Examiner*—Helen M. S. Sneed
*Attorney, Agent, or Firm*—Joel C. Ackerman

[57] ABSTRACT

Compositions which comprise a complex of:
(a) a titanium-containing material having the formula

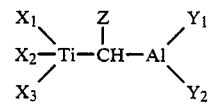

in which $X_1$ is cyclopentadienyl, chlorine, bromine or $C_1$-$C_6$ alkoxy, $X_2$ and $X_3$ are chlorine, bromine, or $C_1$-$C_6$ alkoxy; $Y_1$ and $Y_2$ are chlorine or bromine; and z is hydrogen (preferably) or $C_1$-$C_{10}$ hydrocarbyl are novel reagents for methylenation or analogous reactions with a carbonyl group; and (b) a complexing agent selected from the group consisting of:
  (i) ethers having the formula $R_1OR_2$ in which $R_1$ and $R_2$ are $C_1$-$C_4$ alkyl;
  (ii) cyclic ethers having the formula

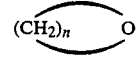

in which n is an integer from 4 to 7; and
  (iii) tertiary amines.

20 Claims, No Drawings

NOVEL TITANIUM-CONTAINING REAGENTS FOR METHYLENATION AND ANALOGOUS REACTIONS

This is a continuation-in-part of U.S. application Ser. No. 818,589, filed Jan. 14, 1986, now abandoned.

BACKGROUND AND PRIOR ART

A series of titanium-containing methylene-bridged compounds having the general formula

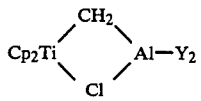

in which the designation "Cp" stands for cyclopentadienyl and Y stands for methyl, chlorine, $CD_3$ or $CH_2C(CH_3)_3$ has been described by Tebbe et al. in a series of articles such as *J.A.C.S.*, 100, 3611–3613 (1978) and 101, 5074–5075 (1979). These compounds are prepared by reaction of dicyclopentadienyl titanium dichloride with trimethylaluminum and are useful as reagents in Wittig reactions, converting the oxygen atom of a carbonyl group to a methylene group. The compounds are effective for methylenation of ketones and esters, as well as unsaturated hydrocarbons, but their use requires long reaction times and the process for their preparation involves trimethylaluminum, which is pyrophoric and requires special handling.

SUMMARY OF THE INVENTION

This invention relates to novel titanium-containing compositions which comprise a complex of:
(a) a titanium-containing material having the formula

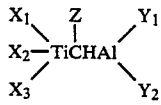

in which $X_1$ is chlorine, bromine, $C_1$–$C_6$ alkoxy or cyclopentadienyl; $X_2$ and $X_3$ are independently chlorine, bromine or $C_1$–$C_6$ alkoxy; $Y_1$ and $Y_2$ are independently chlorine and bromine; and Z is hydrogen or a hydrocarbyl group containing at least 1, and preferably from 1 to 10, carbon atoms; and
  (b) a complexing agent selected from the group consisting of:
    (i) ethers having the formula $R_1OR_2$ in which $R_1$ and $R_2$ are $C_1$–$C_4$ alkyl;
    (ii) cyclic ethers having the formula

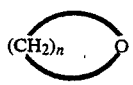

in which n is an integer from 4 to 7; and
    (iii) tertiary amines.

This invention also comprises a process for producing such compositions and processes for reacting certain carbonyl compounds with the titanium-containing composition so as to replace the oxygen atom of the carbonyl group with a methylene or hydrocarbyl group.

The preferred form of this invention further includes compositions in which the titanium-containing material has the formula

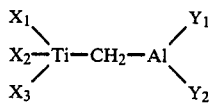

in which $X_1$, $X_2$, $X_3$, $Y_1$ and $Y_2$ are as defined above.

DETAILED DESCRIPTION OF THE INVENTION

This invention relates to novel titanium-containing compositions which are complexes of certain titanium-containing materials with what is generally known in the art as "donor solvents". In the case of the present invention these donor solvents may be selected from three types: dialkyl ethers, that is, ethers having the formula $R_1OR_2$ in which $R_1$ and $R_2$ are each $C_1$–$C_4$ alkyl; cyclic ethers having the formula

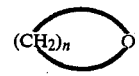

in which n is an integer of from 4 to 7; and tertiary amines.

The titanium-containing materials of these compositions have the general formula

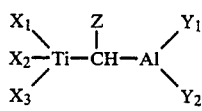

in which $X_1$ is chlorine, bromine, $C_1$–$C_6$ alkoxy or cyclopentadienyl; $X_2$ and $X_3$ are independently chlorine, bromine or $C_1$–$C_6$ alkoxy; $Y_1$ and $Y_2$ are independently chlorine or bromine; and Z is hydrogen or a hydrocarbyl group having from 1 to 10 carbon atoms. The alkoxy groups ($X_1$, $X_2$ and/or $X_3$) may be straight or branched chain and preferably have from 1 to 4 carbon atoms. Examples of such alkoxy groups are methoxy, ethoxy, n-propoxy, isopropoxy and the four butoxy types.

The hydrocarbyl groups represented by Z may be saturated or unsaturated and may be acyclic or may contain a cyclic structure. Acyclic forms of such hydrocarbyl moieties are preferably straight or branched chain alkyl groups having from 1 to 10, preferably 2 to 10, most preferably 2 to 6, carbon atoms. Examples of such groups are methyl, ethyl, n-propyl, n-butyl, n-hexyl, 2-ethylhexyl, n-decyl, etc. If the hydrocarbyl group Z contains a cyclic structure, then the cyclic portion should be separated from the methylene bridging the titanium and aluminum atoms by at least one methylene group. Examples of such cyclical hydrocarbyl groups are benzyl, phenethyl, cyclohexylmethyl and cyclohexylethyl.

Preferred titanium-containing materials have the general formula

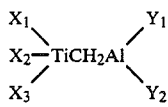

in which, $X_1$, $X_2$, $X_3$, $Y_1$ and $Y_2$ are as defined above (and Z is hydrogen).

The dialkyl ethers contain alkyl groups having from 1 to 4 carbon atoms, such as methyl, ethyl, and the various propyl and butyl groups. The two groups $R_1$ and $R_2$ may be the same or different. Examples of such types of ethers are dimethyl ether, diethyl ether, methyl and propyl ether, methyl and butyl ether, and the like.

The cyclic ethers contain from 4 to 7 carbon atoms in the ring. The most preferred of these is tetrahydrofuran, in which n has a value of 4.

The tertiary amines suitable for use in the compositions of this invention include tertiary (lower alkyl) amines, in which a nitrogen atom is substituted by three alkyl groups (which may be the same or different) having from 1 to 4 carbon atoms apiece, tetraalkyl-alkylene diamines which contain two hydrogen atoms, each substituted by two $C_1$–$C_4$ alkyl groups and linked by an alkylene group having from 1 to 4 carbon atoms, and the heteorcyclic tertiary amine pyridine. Examples of suitable tertiary amines include trimethylamine, triethylamine, tetramethylethylenediamine, and pyridine.

In general, the compositions of this invention contain at least about 2 molar equivalents of complexing agent for each molar equivalent of titanium-containing material. The upper limit of this range would be that in which the novel complexes exist as solutions in the complexing agents or donor solvents. Complexes which have been isolated from such solutions have from about 1 to about 4 molar equivalents of the complexing agent with respect to the amount of titanium-containing material in the complex.

The titanium-containing materials are produced by reaction of a tetra-substituted titanium compound with a methylene-bridged dialane according to the reaction

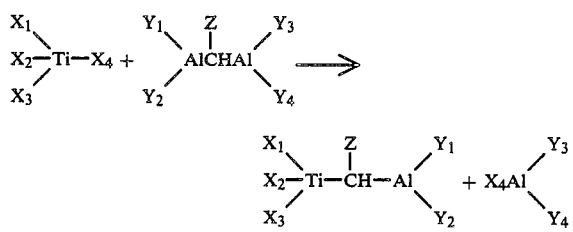

in which $X_4$, $Y_3$ and $Y_4$ are chlorine or bromine.

Starting aluminum-containing materials in which Z is hydrogen may be prepared in the conventional manner by reaction of dihalomethanes such as methylene chloride or methylene bromide or mixtures thereof with metallic aluminum. Starting materials in which Z is a $C_2$–$C_{10}$ group can be prepared by reaction of an aluminum trihalide, a terminal olefin and metallic aluminum, as described in U.S. Pat. No. 4,170,603. Starting materials in which Z is methyl may be prepared as described in Martin et al., *Angewandte Chemie* (International Edition, English), 24, 311 (1985).

The complexes of these titanium-containing materials are preferably produced by carrying out the reaction which produces the titanium-containing materials in the complexing agent as the solvent or as a co-solvent with another solvent such as toluene.

The process may be carried out at room temperature or even below but the formation of the titanium-containing material proceeds slowly at such temperatures. A preferred method of operation is to mix the titanium and aluminum reagents with the complexing agents, e.g., tetrahydrofuran (or mixture of tetrahydrofuran and another solvent) and then heat to about 55° C. for a short time, preferably no more than about 10 or 15 minutes, followed by cooling to room temperature.

The novel complexes may be utilized in the form of the solutions in which they are prepared as above, or may be isolated from the solutions by evaporation of the uncomplexed solvent. This evaporation is generally carried out under vacuum after the reactants have been heated and then cooled. In a preferred embodiment of this invention, the complex is so isolated and is then used to carry out a methylenation (as described below) in another, non-complexing solvent, for instance a hydrocarbon solvent such as toluene. The isolated complexes of this invention are stable materials which can be recovered from the reaction products in this manner. Examples 3–5 which follow show such isolation and subsequent use.

The novel compositions of this invention in which Z is hydrogen function as methylenenating agents for certain carbonyl compounds, specifically ketones having no alpha-hydrogen atoms. Ketones of this type include, for instance, benzophenone, 9-fluorenone and phenyl-tertiary butyl ketone. The presence of alpha-hydrogen atoms in ketones which are treated with the novel compositions of this reaction tend to produce Aldol condensation. The compositions of the present invention containing titanium materials in which Z is a hydrocarbyl group are similarly suitable for replacing the oxygen atom of a carbonyl group of such a ketone with a $C_2$–$C_{11}$ alkyl group (preferably a $C_3$–$C_6$ alkyl group) or cyclic hydrocarbyl groups as defined above, instead of methylene.

The reaction of the carbonyl group with the titanium-containing composition is conducted under similar conditions as is presently performed with "Tebbe" type reagents. The temperature, solvents, etc. will depend on the nature of the carbonyl compound undergoing the reaction as well as the reaction product or products. For instance, aromatic ketones such as benzophenone react quicker at higher temperatures.

Preferred titanium-containing materials in the compositions of the present invention are those in which $X_1$, $X_2$ and $X_3$ are variously $C_1$–$C_4$ alkoxy, chlorine or bromine, Z is hydrogen and $Y_1$ and $Y_2$ are independently chlorine or bromine. These are produced by reaction of titanium tetrahalides, tetraalkoxides, or mixed titanium halide-alkoxide compounds. Among the titanium tetrahalides the preferred reagent is titanium tetrachloride.

The following represent examples of preparation and use of titanium-containing materials pursuant to this invention.

EXAMPLE 1

In a flask there was dissolved 20 millimoles of bis-(dichloroaluminum)methane ($Cl_2AlCH_2AlCl_2$) in 70 milliliters (ml) tetrahydrofuran (THF) at low temperature. A homogeneous solution was formed which was cooled in a dry ice/acetone bath until a white solid precipitated. Then, 10 millimoles of titanium tetrachloride were added dropwise and the solution stirred for approximately 10 minutes at −20° C. Following this, 10 millimoles of benzophenone was added and the reaction mixture was stirred at room temperature for 72 hours. The product was recovered according to conventional techniques; nmr analysis showed that the only reaction product was 1,1-diphenylethylene. Conversion of benzophenone to the diphenylethylene was quantitative.

EXAMPLE 2

The titanium-containing composition was prepared as in Example 1 and THF evaporated under vacuum. The reaction with benzophenone was conducted using 40 ml toluene as the solvent at 90° C. over a period of ½ hour, on the same scale as Example 1. Conversion into 1,1-diphenylethylene was again quantitative.

EXAMPLE 3

(Chemical shifts in this example are in δ (delta) units relative to tetramethylsilane internal standard.)

Fifty millimoles of bis-(dichloroaluminum)methane was dissolved in THF to form 100 ml of solution. Then, 10 ml of this solution (containing 5 millimoles of the aluminum compound) was mixed with 20 ml of a THF solution of titanium tetrachloride, containing 5 millimoles titanium tetrachloride, at room temperature. The reaction mixture was briefly warmed to 55° C., then cooled to room temperature. THF was evaporated under vacuum, leaving a red semi-solid material.

About 0.1 g of the red material was placed into an nmr tube. Deuterated toluene was then added and a clear, dark red solution was formed. The nmr spectrum showed a sharp singlet at −0.50 ppm which was assigned to the methylene bridge between titanium and aluminum. About 0.04 g of benzophenone was added to the nmr tube. After about 5 minutes the nmr spectrum indicated formation of a small amount of 1,1-diphenylethylene at room temperature. The tube was then briefly warmed to about 90° C., and the nmr signal showed that about 25% of the ketone had been converted to the diphenylethylene. At the same time, the signal of the methylene bridge diminished to 75% of its original intensity. The tube was then again warmed and the nmr spectrum showed that at this point benzophenone was almost quantitatively converted to diphenylethylene and the signal at −0.50 ppm disappeared completely. This is evidence that the methylenating agent was a bridging methylene group.

EXAMPLE 4

In a flask, 30 ml of bis-(dichloroaluminum)methane solution in THF (prepared as in Example 3) was mixed with a solution containing 14 millimoles titanium tetrachloride in 50 ml THF. After a brief warming to 55° C., the solution was cooled, THF evaporated under vacuum, and 50 ml toluene added, producing a dark red solution. To this solution there was added 10 millimoles of a triethylaluminum-methyl p-toluate adduct. The adduct had been prepared by dissolving the ester and triethylaluminum in toluene at about 0° C. The reaction mixture was stirred for 72 hours, then hydrolyzed with a small amount of water in the presence of triethylamine and calcium hydroxide buffer. Analysis showed the starting ester was present in a 3:1 ratio to the vinyl ether 1-methoxy, 1-(p-tolyl)ethylene,

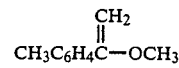

EXAMPLE 5

This example was conducted as in Example 2, on the same scale, except that titanium tetraisopropoxide was used as a starting material instead of titanium tetrachloride. 1,1-Diphenylethylene was formed in 30% yield.

The titanium-containing materials in the compositions of this invention are represented by the formula

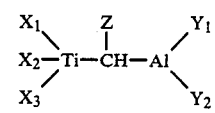

preferably,

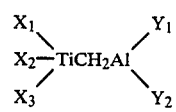

The structure of these is also believed to be linear, as opposed to the double bridging structure of the Tebbe complexes, in which the titanium and aluminum atoms are joined by both methylene and chlorine bridges. The nmr analysis of the titanium-containing material in Example 3 showed a methylene bridge at −0.50 ppm. The Tebbe complex typically shows a methylene group at 8.2 ppm. This difference in spectra indicates the structures of the compounds of this invention are very different from that of the Tebbe complex. The nmr analysis of the reaction of benzophenone indicates that a bridging methylene group was in fact the active methylenating agent in the reaction.

What is claimed:

1. A composition which comprises a complex of:
(a) a titanium-containing material having the formula

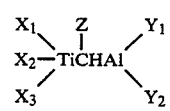

in which $X_1$ is cyclopentadienyl, chlorine, bromine or $C_1$–$C_6$ alkoxy; $X_2$ and $X_3$ are independently chlorine, bromine, or $C_1$–$C_6$ alkoxy; $Y_1$ and $Y_2$ are independently chlorine or bromine; and Z is hydrogen or a $C_1$–$C_{10}$ hydrocarbyl group; and
(b) a complexing agent selected from the group consisting of:
  (i) ethers having the formula $R_1OR_2$ in which $R_1$ and $R_2$ are $C_1$–$C_4$ alkyl;
  (ii) cyclic ethers having the formula

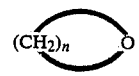

in which n is an integer from 4 to 7; and
(iii) tertiary amines.

2. A composition according to claim 1 in which Z is hydrogen, or a hydrocarbyl group having from 1 to 10 carbon atoms, said hydrocarbyl group being an aliphatic group or having a cyclical portion separated by at least one methylene group from the methylene group bridging the aluminum and titanium atoms.

3. A composition according to claim 2 in which Z is a straight chain alkyl group having from 2 to 6 carbon atoms.

4. A composition according to claim 1 in which Z is hydrogen.

5. A composition according to claim 1 having a linear structure.

6. A composition according to claim 1 in which $X_1$, $X_2$ and $X_3$ are independently chlorine or bromine.

7. A composition according to claim 1 in which at least one of $X_1$, $X_2$ or $X_3$ is $C_1$-$C_6$ alkoxy.

8. A composition according to claim 1 in which at least one of $X_1$, $X_2$ or $X_3$ is $C_1$-$C_4$ alkoxy.

9. A composition according to claim 1 in which $X_1$, $X_2$ and $X_3$ are all $C_1$-$C_4$ alkoxy.

10. A composition according to claim 1 in which the complexing agent is a dialkyl ether having identical alkyl groups.

11. A composition according to claim 10 in which the ether is dimethyl ether.

12. A composition according to claim 10 in which the ether is diethyl ether.

13. A composition according to claim 1 in which the complexing agent is a cyclic ether.

14. A composition according to claim 13 in which the cyclic ether is tetrahydrofuran.

15. A composition according to claim 1 in which the complexing agent is a tertiary amine.

16. A composition according to claim 15 in which the tertiary amine is a trialkyl amine having from 1 to 4 carbon atoms in the alkyl groups.

17. A composition according to claim 15 in which the tertiary amine is a tetra-($C_1$-$C_4$ alkyl)alkylene diamine.

18. A composition according to claim 15 in which the tertiary amine is pyridine.

19. A composition according to claim 1 in which the complexing agent is included in at least two molar equivalents per equivalent of titanium-containing material.

20. A composition according to claim 1 in which the complexing agent is included in an amount of between about 2 and about 4 molar equivalents per equivalent of titanium-containing material.

* * * * *

UNITED STATES PATENT AND TRADEMARK OFFICE
CERTIFICATE OF CORRECTION

PATENT NO. : 4,720,562

DATED : January 19, 1988

INVENTOR(S) : Dennis B. Malpass et al.

It is certified that error appears in the above-identified patent and that said Letters Patent is hereby corrected as shown below:

Title page    "Stauffer Chemical Company, Westport, Conn." should read -- Texas Alkyls, Inc., Deer Park, Texas --.

Signed and Sealed this

Thirtieth Day of August, 1988

Attest:

DONALD J. QUIGG

*Attesting Officer*          *Commissioner of Patents and Trademarks*